United States Patent
Wik et al.

(10) Patent No.: US 9,943,229 B1
(45) Date of Patent: Apr. 17, 2018

(54) SYSTEMS AND METHODS FOR MONITORING PATIENT HEALTH

(71) Applicant: General Electric Company, Schenectady, NY (US)

(72) Inventors: Steven William Wik, Schenectady, NY (US); Timo Tapani Hakala, Helsinki (FI)

(73) Assignee: GENERAL ELECTRIC COPANY, Schenectady, NY (US)

( * ) Notice: Subject to any disclaimer, the term of this patent is extended or adjusted under 35 U.S.C. 154(b) by 0 days.

(21) Appl. No.: 15/372,789

(22) Filed: Dec. 8, 2016

(51) Int. Cl.
*G08C 19/22* (2006.01)
*A61B 5/00* (2006.01)
*H04Q 9/00* (2006.01)

(52) U.S. Cl.
CPC ............ *A61B 5/0024* (2013.01); *H04Q 9/00* (2013.01); *A61B 2560/0209* (2013.01); *H04Q 2209/47* (2013.01)

(58) Field of Classification Search
CPC .................................................. A61B 5/0024
USPC ..................................... 340/870.07
See application file for complete search history.

(56) References Cited

U.S. PATENT DOCUMENTS

| | | | |
|---|---|---|---|
| 7,065,376 B2 | 6/2006 | Wolman et al. | |
| 7,161,926 B2 | 1/2007 | Elson et al. | |
| 9,130,697 B2 | 9/2015 | Struhsaker et al. | |
| 9,232,566 B2 | 1/2016 | Amini et al. | |
| 2008/0031205 A1 | 2/2008 | Kahola et al. | |
| 2011/0221590 A1* | 9/2011 | Baker | A61B 5/0002 340/539.12 |
| 2011/0280224 A1* | 11/2011 | Falck | H04W 72/1215 370/336 |
| 2012/0001751 A1* | 1/2012 | Baker | A61B 5/0024 340/539.12 |
| 2012/0003933 A1* | 1/2012 | Baker | G06F 19/3412 455/41.2 |
| 2012/0134292 A1* | 5/2012 | Pandharipande | H04W 74/0816 370/252 |
| 2012/0275399 A1 | 11/2012 | Liu et al. | |
| 2014/0192696 A1* | 7/2014 | Wang | H04W 72/1252 370/311 |

(Continued)

OTHER PUBLICATIONS

Wang et al., "A Power-Saving Multi-radio Multi-channel MAC Protocol for Wireless Local Area Networks", http://www.fang.ece.ufl.edu/mypaper/infocom06wang.pdf, 2006,pp. 1-12.

(Continued)

*Primary Examiner* — Santiago Garcia
(74) *Attorney, Agent, or Firm* — Pabitra K. Chakrabarti (57) ABSTRACT

Aspects of the invention relate to a system and a method for monitoring health of a patient by using wireless sensor devices positioned to monitor one or more physiological parameters of the patient, and a gateway device in wireless communication with the wireless sensor devices, the wireless sensor devices and the gateway device forming a wireless body area network. The gateway device includes two or more radio frequency integrated circuits (RFICs) connected in at least a series or a parallel connection and provides multiple frequency channels for receiving sensor data from the wireless sensor devices, where the sensor data is transmitted based on time synchronization signals and an multi-channel adaptive protocol.

8 Claims, 4 Drawing Sheets

(56) References Cited

U.S. PATENT DOCUMENTS

2015/0134763 A1* 5/2015 Balakrishnan ...... G06F 9/44505
　　　　　　　　　　　　　　　　　　　　　709/208
2015/0238082 A1* 8/2015 Soro ................... A61B 5/0024
　　　　　　　　　　　　　　　　　　　　　600/300

OTHER PUBLICATIONS

Zhao et al., "SD-MAC: Design and Synthesis of a Hardware-Efficient Collision-Free QoS-Aware MAC Protocol for Wireless Network-on-Chip", IEEE Transactions on Computers, vol. 57, Issue 9, May 30, 2008, pp. 1230-1245.
S.M.Kamruzzaman, "An Energy Efficient Multichannel MAC Protocol for Cognitive Radio Ad Hoc Networks", International Journal of Communication Networks and Information Security (IJCNIS), vol. 2, Issue 2, Aug. 2010, pp. 112-119.
QorIQ Qonverge Portfolio "Next-Generation Wireless Network Bandwidth and Capacity Enabled by Heterogeneous and Distributed Networks", QorIQ Qonverge Platform, freescale.com, 2011, 23 Pages.

* cited by examiner

SYSTEMS AND METHODS FOR MONITORING PATIENT HEALTH

BACKGROUND

This disclosure relates generally to patient health monitoring and more specifically to increasing bandwidth and throughput in a wireless body area network used for patient health monitoring.

A wireless body area network (WBAN) includes wearable computing devices which are often used to monitor a patient's vital signs (e.g., blood pressure, heart rate, oxygen levels, electrocardiogram (ECG) data, etc.) in a hospital's telemetry ward. A wireless personal area network (WPAN) is a short-range network covering a range of about forty feet. The WPAN can be used as a gateway by the WBAN to reach telemetry stations and/or repeaters, so that the monitors can communicate their information to a centralized location.

Because of the critical nature of the information being transmitted by a patient's WBAN, the data outage specifications can require a transmission success rate of, for example, about 95%. Vital sign monitoring is an important part of patient care since the general or particular health of the patient is determined, in part, through measurement and interpretation of key physiological indicators. Such physiological data, however, is only of use if it is transmitted in a timely and accurate manner. Transmission of such vital sign data must therefore be timely and be transmitted at a high rate of success for a WBAN to be beneficial to patient monitoring. Wireless medium in general does not guarantee the reliable data transmission.

BRIEF DESCRIPTION

In one aspect, a system for monitoring health of a patient is described. The system includes wireless sensor devices positioned to monitor one or more physiological parameters of the patient and configured to transmit sensor data representative of the one or more physiological parameters, a gateway device in wireless communication with the wireless sensor devices, and a patient monitoring module configured to receive the sensor data from the gateway device for monitoring the one or more physiological parameters of the patient.

The wireless sensor devices and the gateway device form a wireless body area network, where the gateway device includes two or more radio frequency integrated circuits (RFICs) connected in at least a series or a parallel connection. The wireless sensor devices and the gateway device are configured to communicate with each other based on time synchronization signals and a multi-channel adaptive protocol, characterized by a communication frame structure having at least one beacon time slot for a beacon signal, and frequency separated data slots to communicate with the two or more RFICs based on the multi-channel adaptive protocol.

In another aspect, a method for monitoring health of a patient includes providing wireless sensor devices positioned for monitoring and transmitting one or more physiological parameters of the patient, providing a gateway device in wireless communication with the plurality of wireless sensor devices, the plurality of wireless sensor devices and the gateway device forming a wireless body area network, wherein the gateway device comprises two or more radio frequency integrated circuits (RFICs) connected in at least a series or a parallel connection.

The method includes configuring the wireless sensor devices and the gateway device to communicate with each other based on time synchronization signals and a multi-channel adaptive protocol, characterized by a communication frame structure having at least one beacon time slot for a beacon signal, and frequency separated data slots to communicate with the two or more RFICs based on the multi-channel adaptive protocol.

The method further includes transmitting respective sensor data from the wireless sensor devices to one of the two or more RFICs based on the time synchronization signals and the multi-channel adaptive protocol, and receiving the respective sensor data from the gateway device for monitoring the one or more physiological parameters of the patient.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Aspects disclosed in the specification relate to increasing bandwidth and throughput of data communication in a wireless body area network (WBAN) implemented for monitoring health parameters, referred herein as physiological parameters of a patient. Some non-limiting examples of the physiological parameters include, blood pressure, respiration rate, body temperature, SpO2 (peripheral capillary oxygen saturation), breathing rate, heart rate, pulse rate, blood sugar, calories, fat, acid, EEG (electroencephalogram), and ECG (electrocardiogram).

The WBAN typically includes multiple wireless sensor devices implanted on a patient's body and a gateway to enable communication of sensor data to a hospital infrastructure or any other supervisory health infrastructure. The gateway is implemented using multiple wireless radio frequency integrated circuits (RFICs) running time-synchronized Medium Access Control (MAC) protocols using TDMA (Time Division Multiple Access) architecture. The Medium Access Control (MAC) protocol is used to provide a data link channel for communication between the multiple wireless sensor devices and RFICs. TDMA is a well-known channel access method for shared medium networks. TDMA allows several users to share the same frequency channel by dividing a signal (either a transmitted signal from an RFIC to one or more wireless sensor devices or a received signal by any RFICs received from one or more wireless sensor devices) into different time slots. The users transmit in rapid succession, one after the other, each using its own time slot architecture. The users referred herein, include the multiple wireless sensor devices, RFICs, and any external controllers used in the WBAN network.

In WBAN environment, different data throughput is required in different use cases and for different communication devices that are involved in monitoring the health parameters of the patient. Also, quality of the communication channels varies as a function of time due to signal to noise factors. The method and system described herein, disclose a flexible approach to increase data throughput, as well as, improve communication under low quality conditions.

Figure 1:
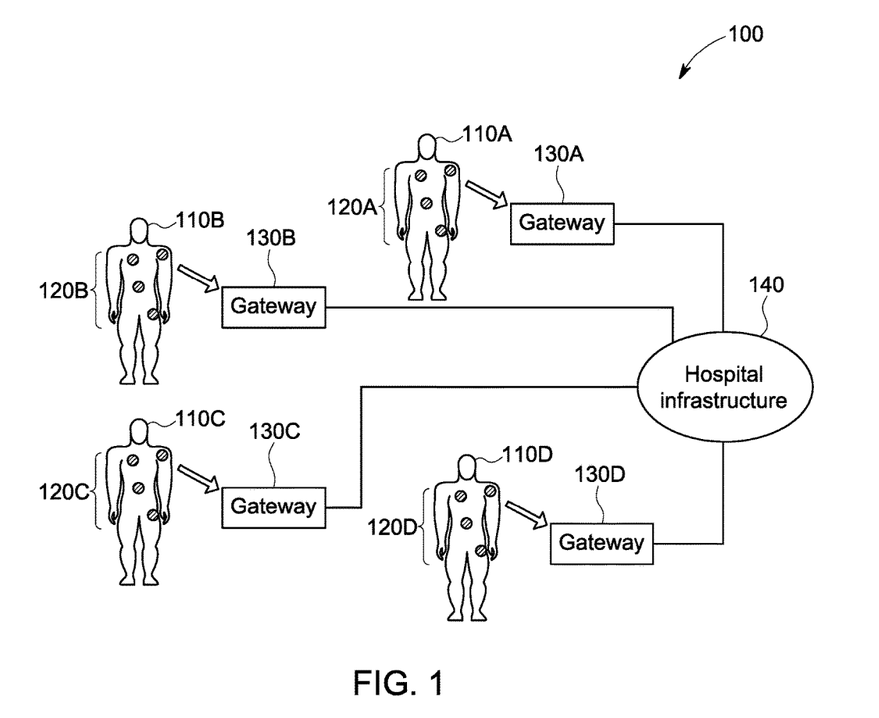
FIG. 1 is a diagrammatic representation of a system for monitoring health of patient in accordance with some embodiments.

FIG. 1 is a diagrammatic representation of a system 100 for monitoring health of a patient in accordance with some embodiments, where each patient is equipped with multiple wireless sensor devices connected in a WBAN that transmits the patient's vital functions. FIG. 1 illustrates multiple patients in a hospital ward, where each patient is linked to a WBAN. Each WBAN includes multiple wireless sensor devices on the patient's body and a gateway device. The gateway device provides time synchronization signals to the sensor devices for its associated WBAN. For each patient 110A, 110B, 110C, 110D a respective WBAN 120A, 120B, 120C, 120D can include sensor device(s) and a respective gateway 130A, 130B, 130C, 130D. The WBANs are connected to hospital infrastructure 140. The hospital infrastructure 140 includes for example, telemetry equipment, bedside monitors, nursing stations, alarms, displays, computers, databases, etc., where the data from the patient can be displayed and interpreted through a monitor or any other graphical user device. FIG. 1 shows one example implementation for WBAN, it will be understood by those skilled in the art that other implementations with different configurations for wireless sensor devices and gateway devices may be possible and are included in the scope of aspects described herein.

Figure 2:
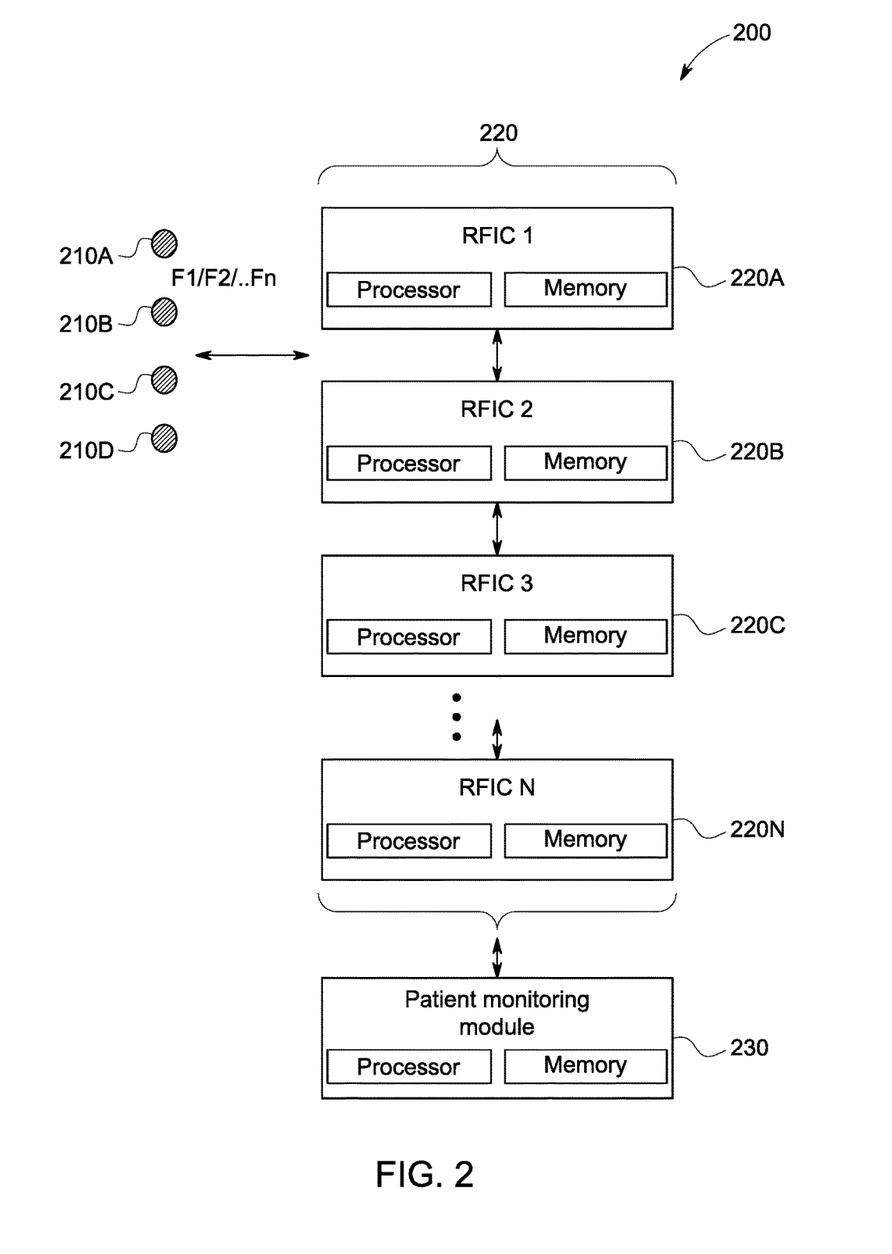
FIG. 2 is a diagrammatic representation of the key components of the system for monitoring health of patient in accordance with some embodiments.

FIG. 2 is a block diagram representation of one specific embodiment for the system 200 for monitoring health of patient showing one set of wireless sensor devices 210A, 210B, 210C, 210D positioned on one patient's body, and sensors 212 A, 212 B, 212 C, 212 D as shown in FIG. 1 to monitor one or more physiological parameters of the patient. A gateway device 220 is in wireless communication with the wireless sensor devices 210A, 210B, 210C, 210D. The gateway device 220 includes two or more radio frequency integrated circuits (RFICs) 220 A, 220 B . . . 220N connected in at least a series or a parallel connection. The gateway device 220 communicates with a patient monitoring module 230 that is configured to receive the patient data from the gateway device 220 for monitoring one or more health parameters of the patient. The patient monitoring module 230, in some implementations, forms a part of the health infrastructure 140 shown in FIG. 1, and also includes a display device such as a monitor or any other a graphical user display (not shown) to display the sensor data representing the physiological parameters. In some implementations, the patient monitoring module 230 is a part of the gateway device itself. In some specific implementations, the sensor data received through the gateway device is communicated to a cloud server or a backend server for remote monitoring and/or data logging for medical records for the patient.

The gateway device 220 as shown in FIG. 2 is configured to provide time synchronization signals to the wireless sensor devices 210A, 210B, 210C, 210D, which are transmitted by a single RFIC as a beacon signal, and to receive sensor data from the different wireless sensor devices. The receiving of the sensor data is advantageously based on a multi-channel adaptive protocol that allows different frequency channels for receiving sensor data from different wireless sensor devices. Each wireless sensor device is configured to transmit respective sensor data to the one of the two or more RFICs based on the time synchronization signals, and an adaptive multi-channel frequency protocol, that is explained in reference to the communication frame structure in FIG. 3 herein below.

Figure 3:
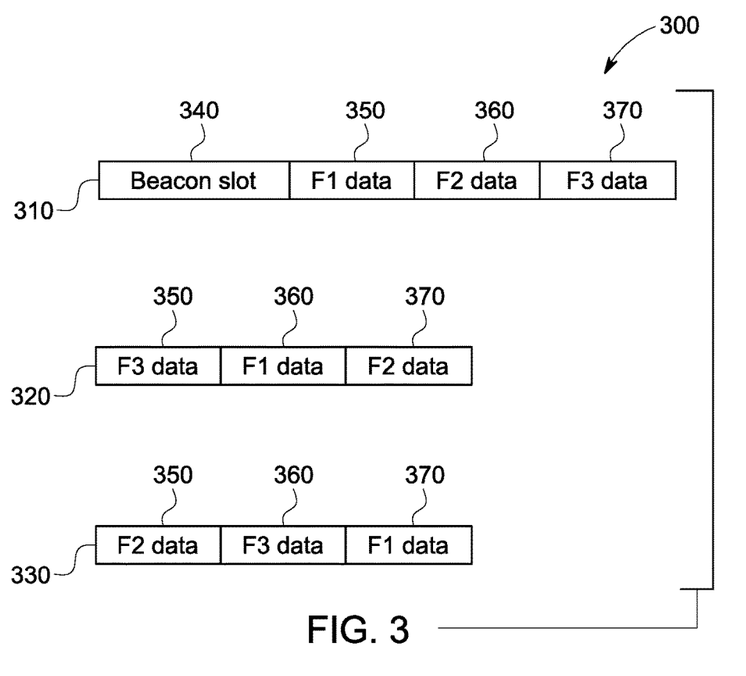
FIG. 3 is diagrammatic representation of a communication frame structure used in the system of FIG. 2, in accordance with some embodiments.

FIG. 3 depicts a communication frame structure 300 in accordance with some embodiments for implementing the multi-channel adaptive protocol referred herein above for three RFICs 310, 320, 330, which are shown as an example. It would be understood by those skilled in the art, that more than three RFICs may be employed based on the data transmission requirements, that may be based on number of wireless sensor devices on each patient, and number of patients, and other such requirements.

Referring to FIG. 3, the communication frame structure 300, sometimes referred herein as a frame, is divided into time periods, called data slots, for example, 340, 350, 360, 370 which have a predetermined, certain duration and are frequency separated, and have a minimum pre-determined spacing to avoid radio frequency interference. Each of the data slots referred herein above can be operated for operated for a different frequency, e.g., frequencies F1, F2, F3, based on the multi-channel adaptive protocol.

In accordance with other implementations, the number of data slots, their duration, and the number of frequencies can be different from the structure depicted in FIG. 3. Additionally, the duration of data slots for different sensor devices can vary.

According to the multi-channel adaptive protocol, the sensor data may be received by at least one RFIC that has free data slots available at the frequency assigned for that particular wireless sensor device for that particular time slot. Thus, the multi-channel adaptive protocol provides a degree of freedom due to availability of two or more RFICs, as well as the availability of assigning different frequencies to different data slots configured in the two or more RFICs.

Further, the multi-channel adaptive protocol also allows simultaneous receipt of the sensor data from more than one wireless sensor devices in the frequency separated data slots in a cascading configuration starting from one of two or more RFICs and successively transmitted to other RFICs of the two or more RFICs based on a hierarchy of available data slots. To enable this, the RFICs are connected in a daisy chain configuration where the received sensor data to a next RFIC goes via a previous RFIC. Referring to FIG. 3, the sensor data to be transmitted to RFIC 320 goes through the previous RFIC i.e. RFIC 310, and so on. This particular configuration of RFICs enables flexible bandwidth scaling in wireless body area network, and allows for a higher and more robust data throughput.

As explained herein above, the data slots 350, 360, 370 are configured to operate at different frequencies F1, F2, F3 and are programmable providing the adaptability for each RFIC, and are used for data transmissions from the wireless sensor devices to the gateway. The data in each of data slots 350, 360, 370 can be from different wireless sensor devices or from the same sensor device but with different data (e.g., blood pressure and pulse rate information from an arterial pressure cuff). In some implementations, the data in the data slots can be the same data from the same wireless sensor device, which is sent redundantly on two different frequencies to increase the probability of receiving at least one of these data successfully.

In the embodiments described herein above, the communication frame structure, has at least one beacon time slot(s) 340 reserved for a beacon signal that is transmitted to the multiple wireless sensor devices. These beacon signals are used for synchronization and control of data transmission from the wireless sensor devices. Each wireless sensor device of a WBAN can listen for the beacon message(s) in the beacon signal sent during the beacon slot period. In accordance with some implementation, each beacon message can contain information for every wireless sensor device.

In one implementation, only one RFIC has the beacon time slot(s) to relay beacon messages to the multiple wireless sensor devices, and is designated as a primary RFIC. Other RFICs have data slots to receive sensor data from the multiple wireless sensor devices.

In another specific implementation, the beacon signal may also be used to configure the two or more RFICs in master-slave configuration, and to operate the gateway as a system-on-a-chip configuration. In the system-on-a-chip configuration, the two or more RFICs have a controller aspect integrated in the circuit, and no external controller is needed for relaying the beacon signal. Further in the system-on-a-chip configuration the RFICs configure themselves for setting up the data flow, where one RFIC is designated as a master, and other as slaves, and the data flow from one RFIC to the other is established based on the master-slave configuration.

In some other implementations, the two or more RFICs are configured to receive an external control input from an external controller (which may be a part of the patient monitoring module shown in FIG. 2, for example) for transmitting the beacon signal to the plurality of wireless sensor devices, and for receiving the sensor data from the plurality of the wireless sensor devices.

Under operation, the beacon signals are sent at the beginning of the communication frame to each wireless sensor device in the patient's WBAN. The beacon signals inform the wireless sensor devices as to which frequencies are to be used for data transmission. During the following time slots, the wireless sensor devices send their sensor data in an assigned time slot to the data slot that is adaptively assigned that frequency.

In accordance with embodiments, not each sensor device of a patient's WBAN need send data in every communication frame. Further, in the implementations referred herein above, when the beacon signal is being transmitted, all other data slots, are in sleep mode (i.e. the RFICs not having the beacon time slot are in sleep mode). Still further, when any RFIC of the two or more RFICs when not in use for data communication with any of the multiple sensor devices, that RFIC switches to a sleep mode. The sleep mode allows for power saving in the above implementations.

In some implementations, the sensor data can have header information. The header information can include information regarding the originator of data, WBAN identification, data collection time, and other details regarding the system, patient, and data.

As referred herein above, one of the advantages of the system and method described herein relates to increased throughput. Throughput referred herein implies number of bits of data per second per data slot. The data communication as described in reference to FIG. 2 and FIG. 3 allows lower data rate per channel, along with increased number of channels.

Increased throughput is explained herein with an example. In prior art, for example, using a single RFIC, a throughput of Y bits/second using Z data slots is achieved. This translates to a throughput of Y/Z bits per data slot. In contrast, in the system and method described herein, if one additional RFIC is used, a throughput of Y bits/seconds is Y/(2*Z) per data slot is achieved, which translates to sending less data per timeslot. This means that we can transmit the data in different ways to increase the performance in low quality wireless conditions.

For example, in some implementations, a wireless bit rate that is 1/X of an original single-RFIC bit rate is used, where X is the number of RFICs connected together, in for example a daisy-chained configuration. A lower data rate per channel achieved in this manner improves robustness in reception of sensor data. A constant rate of data is achieved in some implementations by utilizing two or more simultaneous channels each operating at lower bit rate. In contrast with prior art techniques which usually have one channel with high data rate, the system and method described herein uses multiple channels each with lower data rate to provide better robustness, which leads to better quality of data communication.

In some other implementations, where a low quality condition is due to high RF (radio frequency) interference in prior art techniques, which arises when multiple wireless sensor devices are in close proximity, and are transmitting data at the same time, using the same frequency, causing collisions and therefore data loss. In such conditions, the aspects of system and method described herein which advantageously use multiple RFICs, send the sensor data using the same original data rate, but in smaller packet segments. It would be appreciated by those skilled in the art, that if a packet size for data is decreased, an over-the air time of the wireless signal (complete sensor data) is also decreased, and this reduces a probability of RF interference between multiple wireless sensor devices in close proximity by spreading the data out more over time with large gaps of "free time" in between data segments. This is especially effective in mitigating RF interference with extremely high data rate, and large bandwidth interferers such as WIFI (a facility allowing computers, smartphones, or other devices to connect to the Internet or communicate with one another wirelessly within a particular area), which can interfere with many devices simultaneously, but also sends very short signals (due to high data rate) which are avoided due to the use of multiple RFICs as described herein above.

Figure 4:
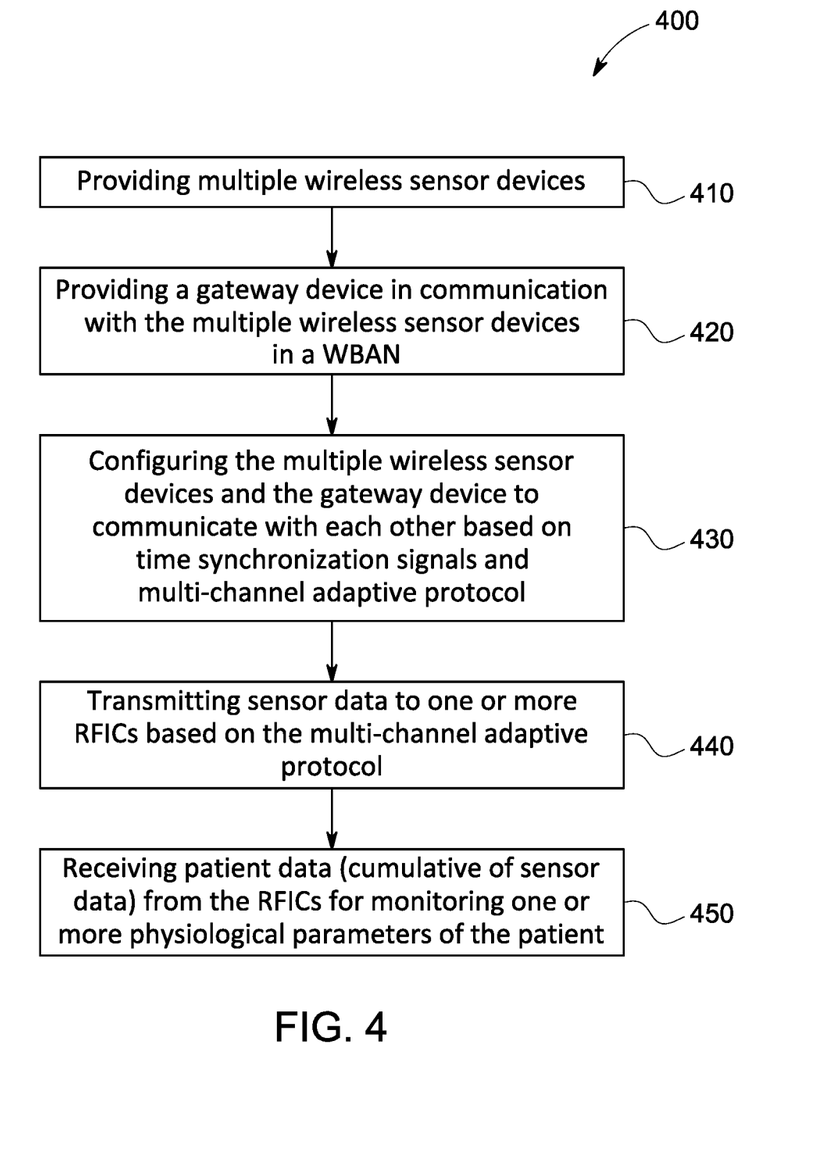
FIG. 4 is a flow chart representation of a method for monitoring health of patient in accordance with some embodiments.

Now in another aspect, a method for monitoring health of patient is provided as shown in flowchart 400 of FIG. 4. The method includes a step 410 for providing multiple wireless sensor devices positioned on a patient's body to monitor and transmit one or more physiological parameters of the patient. The method includes a step 420 for providing a gateway device in wireless communication with the plurality of wireless sensor devices, the plurality of wireless sensor devices and the gateway device forming a wireless body area network, where the gateway device comprises two or more radio frequency integrated circuits (RFICs) connected in at least a series or a parallel connection.

The method includes a step 430 for configuring the gateway device and the plurality of wireless sensor devices for communicating with each other based on time synchronization signals and a multi-channel adaptive protocol characterized by a communication frame structure having at least one beacon time slot for transmitting a beacon signal from one of the two or more RFICs, and several frequency separated data slots for receiving respective sensor data from the wireless sensor devices.

The method includes a step 440 for transmitting respective sensor data representative of the physiological parameters from the wireless sensor devices to one of the two or more RFICs based on the time synchronization signals and the multi-channel adaptive protocol, and a step 450 for receiving the respective patient data, as a cumulative of all the sensor data from the gateway device for monitoring one or more physiological parameters of the patient. Other details of the method are described in the functional aspect of the system of FIGS. 2 and 3, and are similarly implemented in the method aspect.

Overall, the system and method described herein, in some implementations utilizes multiple (two or more) frequency channels using from a set of operating frequency bands, and flexibly adds new frequency channels on a need basis. Example of typical frequency bands include for e.g. 2.4 GHz (Giga Hertz) ISM (Industrial/Scientific/medical) band or country specific MBAN (Medical Body Area Network) bands, well known in the art. In some other implementations, all channels may not be selected from the single frequency band. In a typical implementation, there can be for example, two channels from the country specific MBAN band, and one channel from 2.4 Gz ISM band.

It would be understood by those skilled in the art that the RFICs and the patient monitoring module referred herein above are configured using a processor and a memory. The processor may include at least one arithmetic logic unit, microprocessor, general purpose controller or other processor arrays to perform computations, and/or retrieve data stored on the memory. In one embodiment, the processor may be a multiple core processor. The processor processes data signals and may include various computing architectures including a complex instruction set computer (CISC) architecture, a reduced instruction set computer (RISC) architecture, or an architecture implementing a combination of instruction sets. In one embodiment, the processing capability of the processor may be limited to supporting the retrieval of data and transmission of data. In another embodiment, the processing capability of the processor may also perform more complex tasks, including various types of feature extraction, modulating, encoding, multiplexing, and the like. Other type of processors, operating systems, and physical configurations are also envisioned.

In one embodiment, the memory described herein above may be a non-transitory storage medium. For example, the memory may be a dynamic random access memory (DRAM) device, a static random access memory (SRAM) device, flash memory or other memory devices. The memory may also include a non-volatile memory or similar permanent storage device, and media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices.

In accordance with an embodiment, a computer program application stored in non-volatile memory or computer-readable medium (e.g., register memory, processor cache, RAM, ROM, hard drive, flash memory, CD ROM, magnetic media, etc.) may include code or executable instructions that when executed may instruct and/or cause a controller or processor to perform methods discussed herein such as a method for implementing adaptive frequency protocol, configuring of RFICs, and other aspects of data communication described herein above.

The computer-readable medium may be a non-transitory computer-readable media including all forms and types of memory and all computer-readable media except for a transitory, propagating signal. In one implementation, the non-volatile memory or computer-readable medium may be external memory.

While only certain features of the invention have been illustrated, and described herein, many modifications and changes will occur to those skilled in the art. It is, therefore, to be understood that the appended claims are intended to cover all such modifications and changes as fall within the true spirit of the invention.

The invention claimed is:

1. A system for monitoring health of a patient, the system comprising:
   a plurality of wireless sensor devices positioned to monitor one or more physiological parameters of the patient and configured to transmit sensor data representative of the one or more physiological parameters;
   a gateway device in wireless communication with the plurality of wireless sensor devices, the plurality of wireless sensor devices and the gateway device forming a wireless body area network, wherein the gateway device comprises two or more radio frequency integrated circuits (RFICs) connected in at least a series or a parallel connection; and
   a patient monitoring module configured to receive the sensor data from the gateway device for monitoring the one or more physiological parameters of the patient,
   wherein the gateway device and the plurality of wireless sensor devices are configured to communicate with each other based on time synchronization signals and a multi-channel adaptive protocol characterized by:
   a communication frame structure having at least one beacon time slot for transmitting a beacon signal from one of the two or more RFICs, and a plurality of frequency separated data slots for receiving respective sensor data from a plurality of wireless sensor devices,
   wherein the multi-channel adaptive protocol comprises simultaneous receipt of the sensor data from more than one wireless sensor devices from the plurality of wireless sensor devices in the plurality of frequency separated data slots in a cascading configuration starting from one of two or more RFICs and successively transmitted to other RFICs of the two or more RFICs based on a hierarchy of available data slots.

2. The system of claim 1, wherein the two or more RFICs are configured as a system-on-a-chip configuration for transmitting the beacon signal to the plurality of wireless sensor devices, and for receiving the sensor data from the plurality of the wireless sensor devices.

3. The system of claim 1, wherein the two or more RFICs are configured to receive an external control input for transmitting the beacon signal to the plurality of wireless sensor devices, and for receiving the sensor data from the plurality of the wireless sensor devices.

4. The system of claim 1, wherein any RFIC of the two or more RFICs when not in use, switches to a sleep mode.

5. A method for monitoring health of a patient comprising:
   providing a plurality of wireless sensor devices positioned to monitor one or more physiological parameters of the patient and configured to transmit sensor data representative of the one or more physiological parameters;
   providing a gateway device in wireless communication with the plurality of wireless sensor devices, the plurality of wireless sensor devices and the gateway device forming a wireless body area network, wherein the gateway device comprises two or more radio frequency integrated circuits (RFICs) connected in at least a series or a parallel connection, configuring the gateway device and the plurality of wireless sensor devices for communicating with each other based on time synchronization signals and a multi-channel adaptive protocol characterized by:

a communication frame structure having at least one beacon time slot for transmitting a beacon signal from one of the two or more RFICs, and a plurality of frequency separated data slots for receiving respective sensor data from a plurality of wireless sensor devices, wherein the multi-channel adaptive protocol comprises simultaneous receipt of the sensor data from more than one wireless sensor devices from the plurality of wireless sensor devices in the plurality of frequency separated data slots in a cascading configuration starting from one of two or more RFICs and successively transmitted to other RFICs of the two or more RFICs based on a hierarchy of available data slots;

transmitting respective sensor data from the plurality of wireless sensor devices to one of the two or more RFICs based on the time synchronization signals and the multi-channel adaptive protocol; and receiving the respective sensor data from the gateway device for monitoring the one or more physiological parameters of the patient.

6. The method of claim 5, wherein the transmitting of the beacon signal to the plurality of wireless sensor devices is provided through an RFIC from the two or more RFICs and the transmitting of the beacon signal includes instructions for configuring the two or more RFICs in a master-slave configuration.

7. The method of claim 5, transmitting the beacon signal to the plurality of wireless sensor devices is provided through an external control input.

8. The method of claim 5, wherein any RFIC of the two or more RFICs when not in use, switches to a sleep mode.

\* \* \* \* \*